United States Patent

Nagano et al.

(10) Patent No.: US 9,351,735 B2
(45) Date of Patent: May 31, 2016

(54) INSERTION DEVICE AND INSERTION METHOD OF COIL

(75) Inventors: Yoshitaka Nagano, Iwata (JP); Yukihiro Nishio, Iwata (JP); Takayoshi Ozaki, Iwata (JP)

(73) Assignee: NTN CORPORATION, Osaka (JP)

( * ) Notice: Subject to any disclaimer, the term of this patent is extended or adjusted under 35 U.S.C. 154(b) by 504 days.

(21) Appl. No.: 12/995,113

(22) PCT Filed: Mar. 18, 2009

(86) PCT No.: PCT/JP2009/055256
§ 371 (c)(1),
(2), (4) Date: Nov. 29, 2010

(87) PCT Pub. No.: WO2009/144995
PCT Pub. Date: Dec. 3, 2009

(65) Prior Publication Data
US 2011/0077681 A1    Mar. 31, 2011

(30) Foreign Application Priority Data
May 29, 2008 (JP) .................. 2008-140990

(51) Int. Cl.
*A61M 29/00* (2006.01)
*A61B 17/12* (2006.01)
(Continued)

(52) U.S. Cl.
CPC ....... *A61B 17/12022* (2013.01); *A61B 17/1214* (2013.01); *A61B 17/12113* (2013.01);
(Continued)

(58) Field of Classification Search
CPC ............ A61M 25/0013; A61M 25/01; A61M 25/0113; A61M 25/0105; A61M 25/0116; A61M 25/0169; A61M 25/0172; A61M 25/09;
(Continued)

(56) References Cited

U.S. PATENT DOCUMENTS 5,108,407 A    4/1992  Geremia et al.
6,096,004 A *  8/2000  Meglan et al. ............. 604/95.01
(Continued)

FOREIGN PATENT DOCUMENTS

JP    59-181122    10/1984
JP    2000-042116    2/2000
(Continued)

OTHER PUBLICATIONS

European Search Report issued in European Application No. 09754503.2 issued on Sep. 17, 2012.

*Primary Examiner* — Jonathan W Miles
*Assistant Examiner* — Kendra Obu
(74) *Attorney, Agent, or Firm* — McDermott Will & Emery LLP

(57) ABSTRACT

An insertion device of a coil includes a delivery wire driving unit, a secondary catheter driving unit, and a control circuit. A platinum coil for coil embolization is attached to the tip of a delivery wire. The delivery wire driving unit is provided in the proximity of the entrance of a Y connector such that the delivery wire is advanced and moved back. The secondary catheter driving unit is provided in the proximity of the entrance of a Y connector such that the secondary catheter is advanced and moved back. The control circuit controls the delivery wire driving unit so as to insert the delivery wire by a predetermined insertion force. If the delivery wire cannot be inserted, the control circuit controls the secondary catheter driving unit such that the secondary catheter is advanced after being moved back, and then controls the delivery wire driving unit so as to insert the delivery wire.

11 Claims, 10 Drawing Sheets

(51) Int. Cl.
*A61M 25/01* (2006.01)
*A61M 25/09* (2006.01)
*A61B 17/00* (2006.01)

(52) U.S. Cl.
CPC ............ *A61M25/01* (2013.01); *A61M 25/0105* (2013.01); *A61M 25/0113* (2013.01); *A61M 25/09041* (2013.01); *A61B 2017/00398* (2013.01); *A61B 2017/1205* (2013.01)

(58) Field of Classification Search
CPC .................. A61M 25/09041; A61M 25/0905; A61M 25/0122; A61M 25/0133; A61M 2025/015; A61M 2025/0175; A61M 2025/0177; A61M 2025/09058; A61M 2025/0166; A61B 17/12109; A61B 17/12113; A61B 2017/00398; A61B 2017/1205; A61B 2017/12127; A61B 2017/00367; A61B 2017/00371; A61B 2017/00376; A61B 2017/0038; A61B 2017/00384; A61B 2017/00389; A61B 2017/00393; A61B 2017/00402; A61B 2017/00411; A61B 2017/00592; A61B 2017/0061; A61B 2017/00623; A61B 2017/00632; A61B 2017/00646; A61B 2017/00659; A61B 2017/00725; A61B 2017/0073; A61B 2017/00734; A61B 2017/00778; A61B 17/12131; A61B 17/1214; A61B 17/12145; A61B 17/1215; A61B 17/12154; A61B 17/12163; A61B 17/12168; A61B 17/12172; A61B 17/12177; A61B 2017/12054; A61B 2017/12059; A61B 2017/12063; A61B 2017/12068; A61B 2017/12072; A61B 2017/12077; A61B 2017/12081; A61B 2017/12086; A61B 2017/1209; A61B 2017/12095; A61B 17/12099; A61B 17/12118; A61B 17/12122; A61B 17/0057; A61B 17/12022; A61B 17/12027; A61B 17/12031; A61B 17/12036; A61B 17/1204; A61B 17/12045; A61B 19/22; A61B 19/2203; A61B 19/46; A61B 2019/2207; A61B 2019/2211; A61B 2019/2215; A61B 2019/2219; A61B 2019/2223; A61B 2019/2226; A61B 2019/223; A61B 2019/2296; A61B 2019/461; A61B 2019/462; A61B 2019/464; A61B 2019/465; A61B 2019/466; A61B 2019/467; A61B 2017/00057; A61B 2017/00061; A61B 2017/00066; A61B 2017/0007; A61B 2017/0011; A61B 2562/0233; A61B 2562/0242; A61B 2562/0266; A61B 8/4254; A61B 8/4263; A61B 5/06; A61B 5/061; A61B 5/063; A61B 5/064; A61B 5/065; A61B 5/066; A61B 5/1455; A61B 5/14552; A61B 25/0169; A61B 25/0172; B25J 9/065; B25J 9/10; B25J 9/101; B25J 9/161602; B25J 9/1628; B25J 9/1633; B25J 9/1638; B25J 9/1648; B25J 9/1651
USPC .................... 606/1, 108, 129–130, 205–209; 604/93.01, 95.01, 156, 528; 623/1.11
See application file for complete search history.

(56) References Cited

U.S. PATENT DOCUMENTS

| | | | |
|---|---|---|---|
| 6,272,371 B1 * | 8/2001 | Shlomo ......................... | 600/424 |
| 6,726,675 B1 | 4/2004 | Beyar | |
| 2002/0177789 A1 | 11/2002 | Ferry et al. | |
| 2005/0192621 A1 * | 9/2005 | Wallace et al. ............... | 606/200 |
| 2005/0272971 A1 * | 12/2005 | Ohnishi ............ | A61B 1/00009 600/101 |
| 2006/0095022 A1 * | 5/2006 | Moll et al. ........................ | 606/1 |
| 2007/0060879 A1 | 3/2007 | Weitzner et al. | |
| 2007/0173861 A1 * | 7/2007 | Strommer et al. ............. | 606/108 |
| 2007/0287992 A1 * | 12/2007 | Diolaiti et al. .................... | 606/1 |
| 2010/0030115 A1 * | 2/2010 | Fujimoto et al. ............... | 600/587 |

FOREIGN PATENT DOCUMENTS

| | | |
|---|---|---|
| JP | 2000-512515 | 9/2000 |
| JP | 2001-157662 | 6/2001 |
| WO | WO 97/19643 | 6/1997 |
| WO | WO 9945994 A1 * | 9/1999 |

* cited by examiner

INSERTION DEVICE AND INSERTION METHOD OF COIL

RELATED APPLICATIONS

This application is the U.S. National Phase under 35 U.S.C. §371 of International Application No. PCT/JP2009/055256, filed on Mar. 18, 2009, which in turn claims the benefit of Japanese Application No. 2008-140990, filed on May 29, 2008, the disclosures of which Applications are incorporated by reference herein.

TECHNICAL FIELD

The present invention relates to an insertion device and an insertion method of a coil. Particularly, the present invention relates to the technique of inserting a coil attached to the tip of a delivery wire for embolization treatment of a cerebral aneurysm.

BACKGROUND ART

Treatment using a minimally invasive catheter is conventionally carried out. For example, FIG. 12 shows a medical instrument employed in the coil embolization treatment of a cerebral aneurysm that is the cause of subarachnoid bleeding. A platinum coil for coil embolization is attached to the head of a delivery wire. This delivery wire and a catheter are inserted into a Y connector. The catheter is hollow. The delivery wire is inserted in the hollow region of the catheter. The surgeon manipulates the delivery wire and catheter in the proximity of the entrance of the Y connector.

Medical treatment based on a catheter requires skill, and the manipulation of the catheter or delivery wire requires critical control. For the purpose of improving the handling of the catheter and delivery wire in medical treatment based on a catheter, a master slave apparatus as disclosed in Japanese Patent Laying-Open Nos. 2000-42116 and 2001-157662 is proposed.

Patent Document 1: Japanese Patent Laying-Open No. 2000-42116
Patent Document 2: Japanese Patent Laying-Open No. 2001-157662

DISCLOSURE OF THE INVENTION

Problems to be Solved by the Invention

At the master slave apparatus, the surgeon operates the manipulation unit of the master unit. A roller or sphere at the slave unit is rotated by a motor or the like corresponding to the movement of the manipulation unit at the master unit. In order to insert the coil into the aneurysm without applying excessive insertion force thereto, the insertion force detected at the slave is applied as a sense of force for the operator of the master unit at the master slave apparatus. One possible approach to avoid excessive insertion force of the delivery wire is to increase the sense of force for the operator.

However, if the sense of force for the operator is increased, a sense of force greater than the actual insertion force of the delivery wire may be applied to the operator. Accordingly, the operator may stop the insertion of the delivery wire although the insertion force of the delivery wire is not so great. In this case, an insertion force required to insert the coil attached to the tip of the delivery wire into the aneurysm cannot be achieved.

The present invention is directed to solving the problem set forth above. An object of the present invention is to insert a coil with favorable accuracy.

Means for Solving the Problems

An insertion device of a coil according to an aspect is directed to an insertion device of a coil attached to the tip of a delivery wire. The insertion device includes a first driving unit moving a catheter into which a delivery wire is inserted, a second driving unit moving the delivery wire, and a control unit controlling the second driving unit so as to insert the delivery wire by a predetermined insertion force, and controlling the first driving unit such that the catheter is advanced after the catheter is moved back if the delivery wire cannot be inserted under a state where the second driving unit is controlled so as to insert the delivery wire by the predetermined insertion force, and controlling the second driving unit such that the delivery wire is inserted by the predetermined insertion force after the catheter is advanced.

According to the configuration, the delivery wire is inserted by a predetermined insertion force. If the delivery wire cannot be inserted, the catheter is moved back, and then advanced. Accordingly, the position of the tip of the catheter in the aneurysm can be changed. Subsequently, the delivery wire is inserted. Therefore, the aneurysm can be filled evenly with the coil. As such, the catheter and delivery wire can be inserted automatically without depending on the manipulation by a surgeon or the like while the insertion force of the delivery wire is controlled with favorable accuracy as compared to the case where insertion is carried out manually. As a result, the wire provided at the tip of the delivery wire can be inserted with favorable accuracy.

Preferably, the control unit controls the first driving unit and the second driving unit such that the delivery wire is advanced while the catheter is retreated, and the delivery wire is retreated while the catheter is advanced.

According to the configuration, the delivery wire is advanced during moving back of the catheter. Therefore, the delivery wire can be prevented from moving back in conjunction with the catheter. Further, the delivery wire is moved back during advancement of the catheter. Accordingly, the delivery wire can be prevented from advancing in conjunction with the catheter. Thus, the position of the coil can be maintained.

Further preferably, the control unit increases the distance of moving back and advancement of the catheter if moving back and advancement of the catheter are repeated by a predetermined number of times.

In the case where the moving back and advancement of the catheter is repeated for the predetermined number of times according to the configuration, it is likely that the bending of the catheter is merely spread by the catheter being moved back, and the position of the tip of the catheter in the aneurysm has not changed. In this context, the distance of moving back and advancement of the catheter is increased so that the catheter is moved more than the bending of the catheter. Accordingly, the position of the tip of the catheter in the aneurysm can be changed. Then, the delivery wire is inserted. Thus, the aneurysm can be filled evenly with the coil.

Further preferably, the control unit stops insertion of the delivery wire when the distance of moving back and advancement the catheter reaches a predetermined distance.

According to the configuration, there is a possibility of the tip of the catheter exiting from the aneurysm when the distance of moving back and advancement of the catheter reaches the predetermined distance. In this case, a determination is made that insertion of the coil is not possible, and insertion of the delivery wire, i.e. insertion of the coil, is stopped. This prevents the tip of the catheter from exiting from the aneurysm.

Further preferably, the control unit reduces the insertion force of the delivery wire when the speed of inserting the delivery wire is higher than a predetermined speed.

This configuration allows the insertion force of the delivery wire to be reduced when the speed of inserting the delivery wire exceeds a predetermined speed. Accordingly, slippage between the delivery wire and the roller feeding out the delivery wire can be suppressed. Therefore, the inserted length of the delivery wire can be calculated with favorable accuracy based on the number of rotations of the roller, or the like.

Further preferably, the control unit stops insertion of the delivery wire when the inserted length of the delivery wire reaches a predetermined length.

The configuration allows insertion of the delivery wire to be stopped when the inserted length of the delivery wire reaches the predetermined length. Accordingly, the entire length of the coil inserted in the aneurysm can be controlled with favorable accuracy.

Further preferably, the second driving unit drives the delivery wire through the rotation of a motor. The control unit calculates the insertion force of the delivery wire from at least one of a current value of the motor and a bending degree of the delivery wire.

The configuration allows the insertion force of the delivery wire to be calculated with favorable accuracy from the current value of the motor driving the delivery wire or the bending degree of the delivery wire.

Further preferably, the insertion device further includes, instead of the control unit, a device controlling the first driving unit and the second driving unit according to manipulation by the operator.

The configuration allows the catheter and delivery wire to be inserted reflecting manipulation by a surgeon, for example, according to the status.

Effects of the Invention

According to the present invention, insertion of a coil provided at the tip of a delivery wire can be performed with favorable accuracy.

Figure 1:
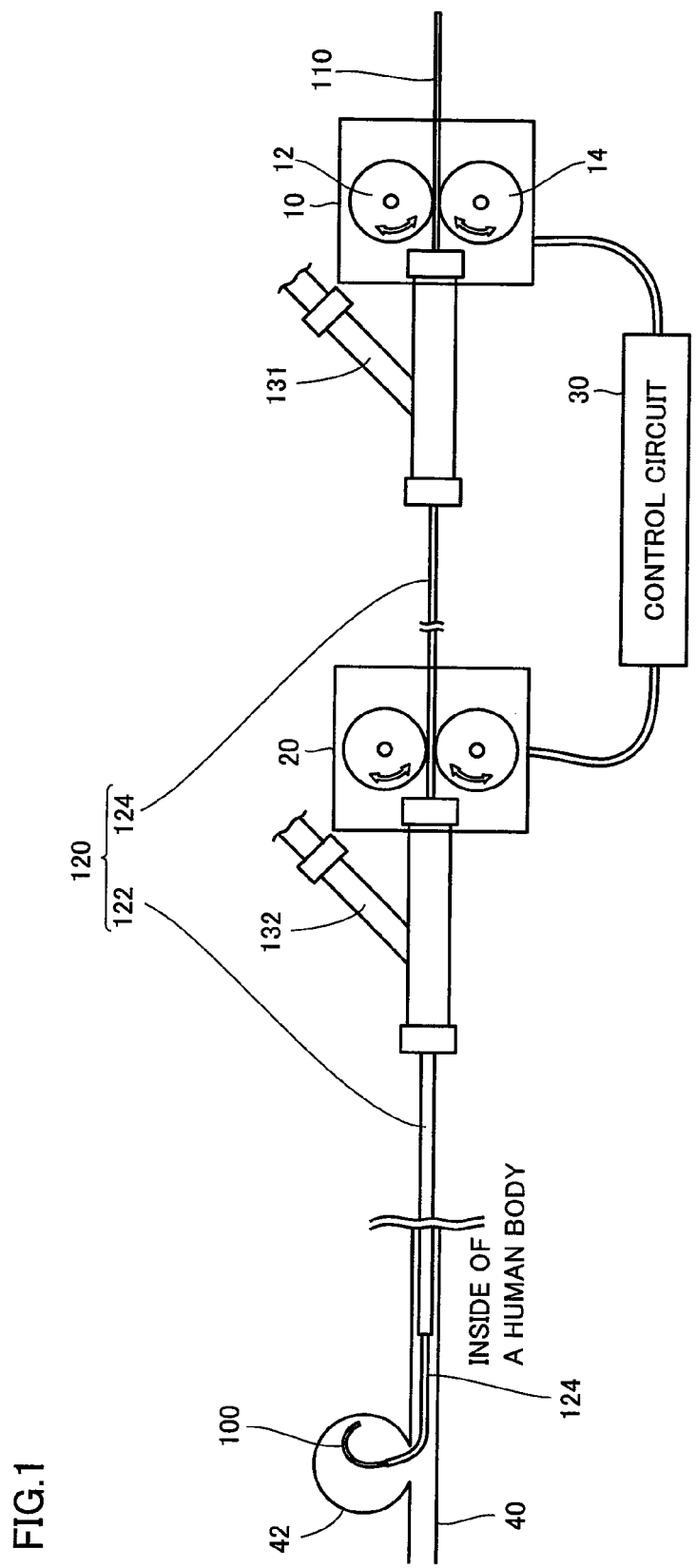
FIG. 1 represents a schematic configuration of an insertion device of a coil.

DESCRIPTION OF THE REFERENCE NUMBERS 10 delivery wire driving unit; 12 pressing roller; 14 feeding roller; 16 motor; 18 encoder; 20 secondary catheter driving unit; 30 control circuit; 40 blood vessel; 42 aneurysm; 50 measurement instrument; 52 space; 60 master device; 62 delivery wire manipulation unit; 64 secondary catheter manipulation unit; 100 platinum coil; 110 delivery wire; 120 catheter; 122 primary catheter; 124 secondary catheter; 131, 132 Y connector; 140 constant current source.

BEST MODES FOR CARRYING OUT THE INVENTION

Embodiments of the present invention will be described hereinafter with reference to the drawings. In the following, the same elements have the same reference characters allotted. Their designation and function are also identical. Therefore, detailed description thereof will not be repeated.

First Embodiment

An insertion device of a coil according to a first embodiment of the present invention will be described hereinafter. As shown in FIG. 1, an insertion device of a coil includes a delivery wire driving unit 10, a secondary catheter driving unit 20, and a control circuit 30.

By way of example, the present embodiment will be described based on an insertion device as a medical instrument employed in the coil embolization treatment of an aneurysm 42 developed at a blood vessel 40 in the brain. The application of the insertion device is not limited to the coil embolization treatment of an aneurysm 42.

A platinum coil 100 for coil embolization is attached at the tip of a delivery wire 110. Delivery wire 110 and a catheter 120 are inserted in Y connectors 131 and 132, respectively.

Catheter 120 includes a primary catheter 122 and a secondary catheter 124. Primary catheter 122 and secondary catheter 124 are hollow. Secondary catheter 124 is inserted in the hollow region of primary catheter 122. Delivery wire 110 is inserted in the hollow region of secondary catheter 124.

Figure 2:
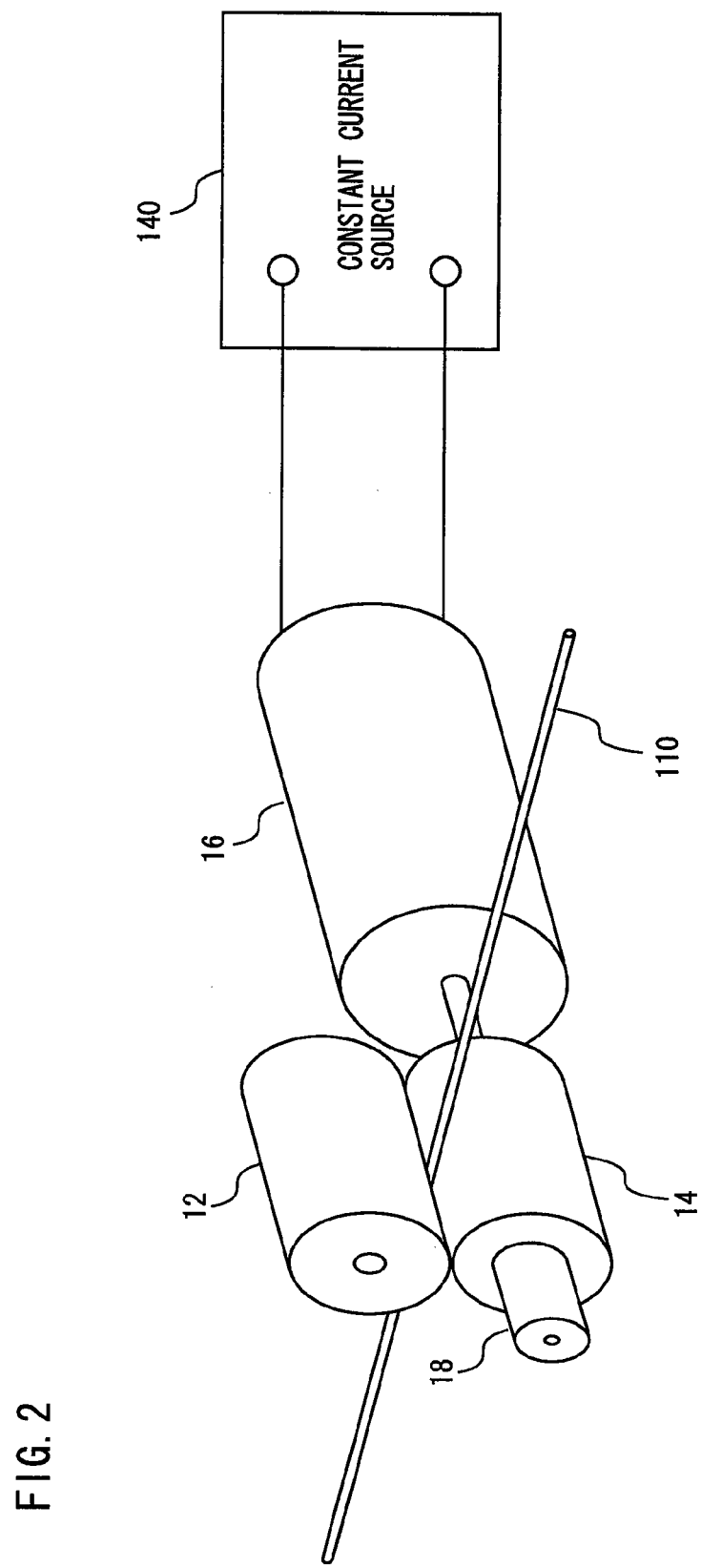
FIG. 2 is a perspective view of a delivery wire driving unit.

A delivery wire driving unit 10 is provided in the proximity of the entrance of Y connector 131 such that delivery wire 110 is advanced and moved back. Delivery wire driving unit 10 includes a pressing roller 12, a feeding roller 14, and a motor 16, as shown in FIG. 2.

Pressing roller 12 and feeding roller 14 are provided so as to sandwich delivery wire 110 therebetween. Feeding roller 14 is coupled to motor 16. Feeding roller 14 is preferably coupled directly to the rotor of motor 16 without any speed reducer or the like.

Motor 16 is driven by a current supplied from a constant current source 140. The driving force of motor 16, i.e. the insertion force of platinum coil 100 (delivery wire 110), is determined according to the value of the current of motor 16. Therefore, in the present embodiment, the insertion force of platinum coil 100 (delivery wire 110) is determined by defining the current value of motor 16.

The number of rotations (accumulated number of rotations) and the rotating speed of feeding roller 14 are detected by an encoder 18. A signal representing the detected result is input to control circuit 30. Control circuit 30 calculates the insertion amount (travel distance) of delivery wire 110 by multiplying the circumference of feeding roller 14 by the number of rotations of feeding roller 14, for example.

Secondary catheter driving unit 20 has a configuration similar to that of delivery wire driving unit 10. Secondary catheter driving unit 20 is provided in the proximity of the entrance of Y connector 132 such that secondary catheter 124 is advanced and moved back.

Control circuit 30 controls delivery wire driving unit 10 and secondary catheter driving unit 20 so as to move delivery wire 110 and secondary catheter 124 in a predetermined manner.

In the present embodiment, control circuit 30 controls delivery wire driving unit 10 and secondary catheter driving unit 20 such that delivery wire 110 is moved by a predetermined insertion force to insert platinum coil 100 into aneurysm 42 by executing a program stored in a storage medium such as a ROM (Read Only Memory), CD (Compact Disc), DVD (Digital Versatile Disc), and the like.

An insertion force of delivery wire 110 is set at an optimum value to allow platinum coil 100 in aneurysm 42 to be inserted into aneurysm 42 without damage to blood vessel 40, taking into account the flexibility of blood vessel 40, and the like.

Figure 3:
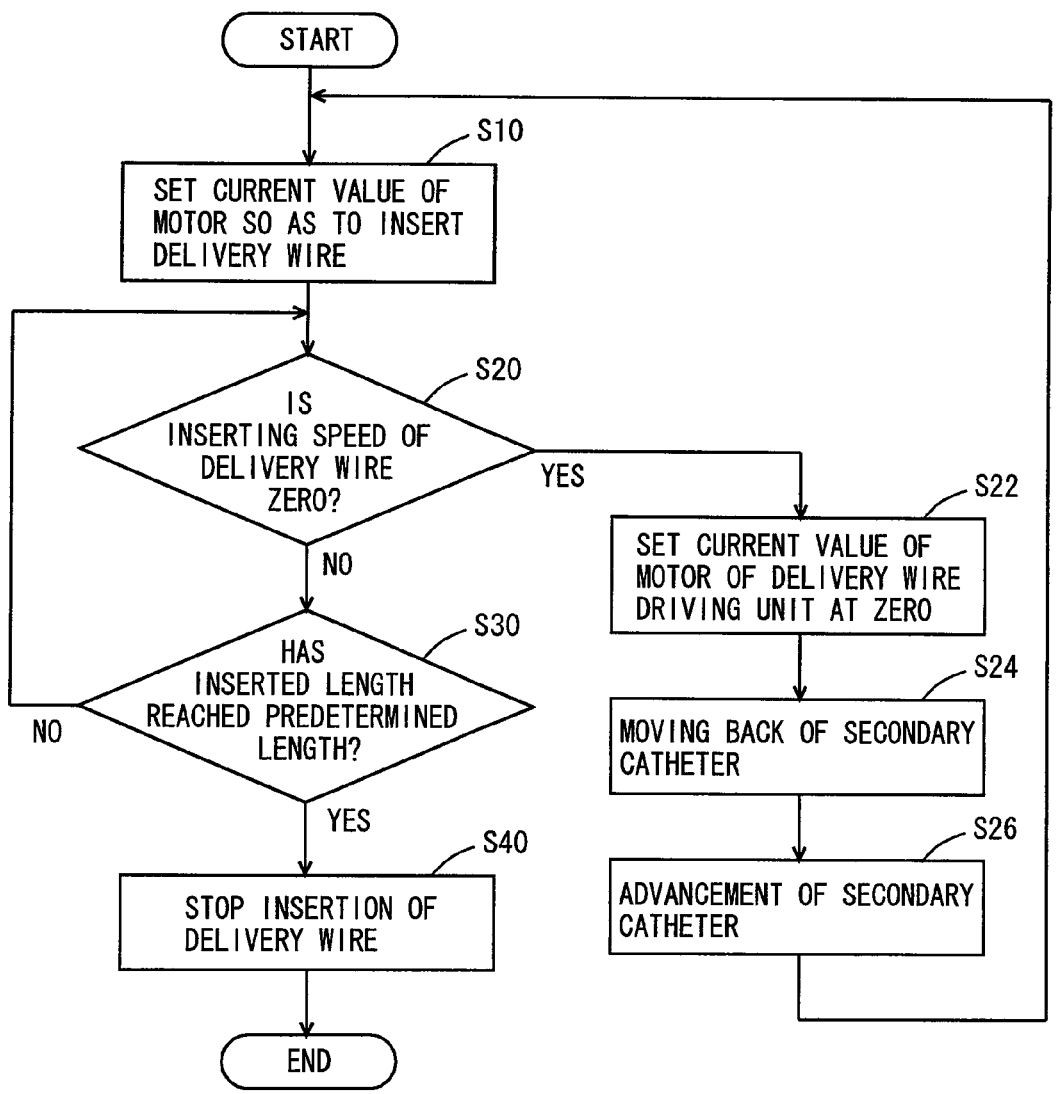
FIG. 3 is a flowchart of the control structure of a program executed by a control circuit according to a first embodiment.

A control structure of a program executed by control circuit 30 of the present embodiment will be described with reference to FIG. 3.

At step (hereinafter, step abbreviated as S) 10, control circuit 30 sets the current value of motor 16 of delivery wire driving unit 10, i.e. the torque of motor 16, such that delivery wire 110 is inserted into secondary catheter 124 by a predetermined insertion force.

At S20, control circuit 30 determines the rotating speed of feeding roller 14 of delivery wire driving unit 10, i.e. whether the inserting speed of delivery wire 110 is zero or not. When the rotating speed of feeding roller 14 of delivery wire driving unit 10 is zero (YES at S20), control proceeds to S22; otherwise (NO at S20), control proceeds to S30.

At S22, control circuit 30 sets the current value of motor 16 of delivery wire driving unit 10, i.e., the torque, at zero.

At S24, control circuit 30 controls secondary catheter driving unit 20 such that secondary catheter 124 is moved back by just a predetermined distance. At S26, control circuit 30 controls secondary catheter driving unit 20 such that secondary catheter 124 is advanced by just the predetermined distance, preferably, a distance equal to the moved back distance.

At S30, control circuit 30 determines whether the inserted length of delivery wire 110 has reached a predetermined length. When the inserted length of delivery wire 110 reaches the predetermined length (YES at S30), control proceeds to S40; otherwise (NO at S30), control returns to S20.

At S40, control circuit 30 stops insertion of delivery wire 110.

An operation of the coil insertion device according to the present embodiment, based on the configuration and flowchart set forth above, will be described hereinafter.

In order to insert platinum coil 100 into aneurysm 42, the current value of motor 16 of delivery wire driving unit 10, i.e. the torque of motor 16, is set such that delivery wire 110 is inserted at a predetermined insertion force (S10).

As such, delivery wire 110 can be inserted automatically without having to depend on manipulation by a surgeon or the like. Therefore, delivery wire 110 can be inserted while the insertion force of delivery wire 110 is controlled with favorable accuracy as compared to the case where insertion is carried out manually by a surgeon or the like. As a result, insertion of platinum coil 100 provided at the tip of delivery wire 110 can be performed with favorable accuracy without excessive insertion force applied to aneurysm 42.

Figure 4:
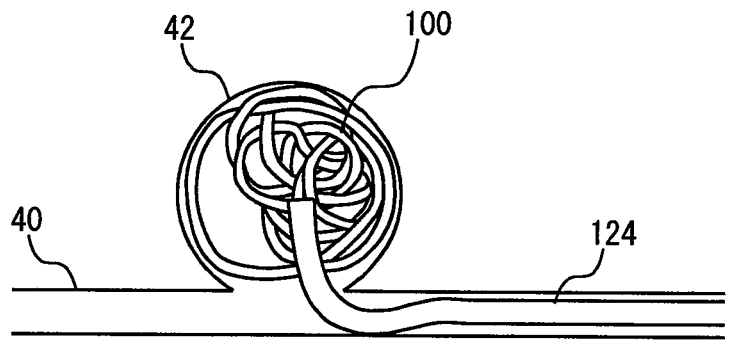
FIG. 4 is a (first) diagram representing a platinum coil and a secondary catheter.

It is to be noted that, when delivery wire 110 is inserted by a predetermined insertion force, the inserting resistance is increased according to the amount of platinum coil 100 present in aneurysm 42. When the inserting resistance becomes greater than the insertion force, the rotating speed of feeding roller 14 of delivery wire driving unit 10, i.e. the inserting speed of delivery wire 110, becomes zero (YES at S20), as shown in FIG. 4.

Figure 5:
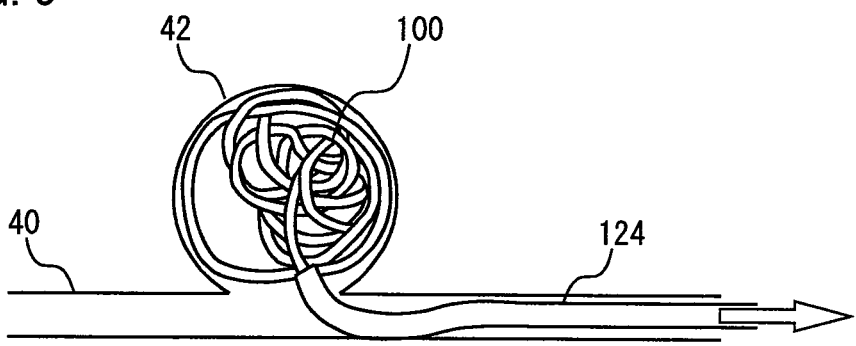
FIG. 5 is a (second) diagram representing a platinum coil and a secondary catheter.

In this case, the current value of motor 16 of delivery wire driving unit 10, i.e. the torque, is set at zero (S22). In other words, insertion of delivery wire 110 is temporarily stopped. Furthermore, as shown in FIG. 5, secondary catheter driving unit 20 is controlled such that secondary catheter 124 is moved back by just a predetermined distance (S24).

Figure 6:
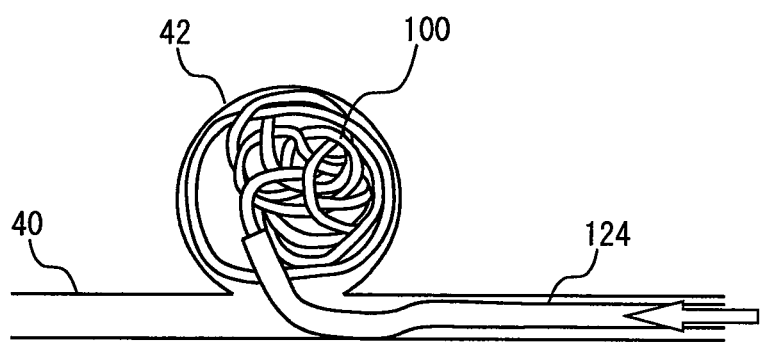
FIG. 6 is a (third) diagram representing a platinum coil and a secondary catheter.

Subsequently, as shown in FIG. 6, secondary catheter driving unit 20 is controlled such that secondary catheter 124 advances by just a predetermined distance (S26). When secondary catheter 124 is placed back, there is a possibility of the tip portion of secondary catheter 124 being located at a position where the density of platinum coil 100 is low, differing from the position before secondary catheter 124 is pulled. Therefore, the inserting resistance of platinum coil 100 is reduced to allow re-insertion of delivery wire 110.

Thus, the current value of motor 16 of delivery wire driving unit 10, i.e. the torque of motor 16, is set such that delivery wire 110 is inserted by a predetermined insertion force (S10).

The length of platinum coil 100 inserted into aneurysm 42 is determined. Therefore, when the inserted length of delivery wire 110 reaches a predetermined length (YES at S30), insertion of delivery wire 110 is stopped (S40).

Second Embodiment

A second embodiment of the present invention will be described hereinafter. The present embodiment differs from the previous first embodiment in that, if delivery wire 110 cannot be inserted into aneurysm 42 even after repeating moving back and advancement of secondary catheter 124 by a predetermined number of times, the distance of moving back and advancement of secondary catheter 124 is increased. The remaining structure is identical to that of the first embodiment set forth above. Therefore, detailed description thereof will not be repeated.

Figure 7:
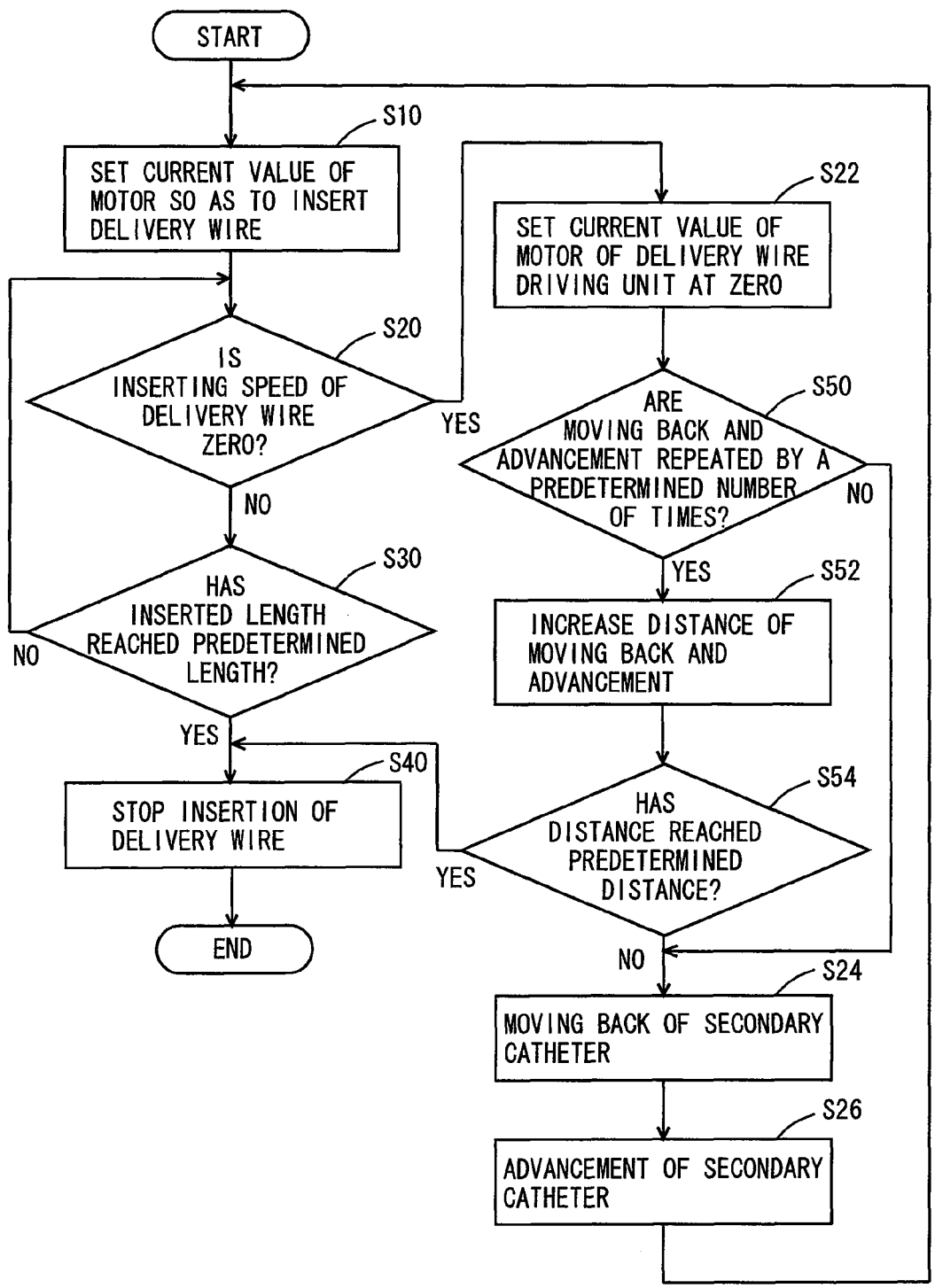
FIG. 7 is a flowchart of the control structure of a program executed by a control circuit according to a second embodiment.

A control structure of the program executed by control circuit 30 according to the present embodiment will be described hereinafter with reference to FIG. 7. The processes identical to those in the program of the previous first embodiment have the same step number allotted. Therefore, detailed description thereof will not be repeated.

At S50, control circuit 30 determines whether moving back and advancement of secondary catheter 124 have been repeated for a predetermined number of times. If moving back and advancement of secondary catheter 124 have been repeated for a predetermined number of times (YES at S50), control proceeds to S52; otherwise (NO at S50), control proceeds to S24.

At S52, control circuit 30 increases the distance of moving back and advancement of secondary catheter 124 by just a predetermined distance.

At S54, control circuit 30 determines whether the distance of moving back and advancement of secondary catheter 124 have reached a predetermined length or not. When the distance of moving back and advancement of secondary catheter 124 has reached a predetermined length (YES at S54), control proceeds to S40; otherwise (NO at S54), control proceeds to S24.

An operation of the coil insertion device according to the present embodiment, based on the configuration and flowchart set forth above, will be described hereinafter.

Secondary catheter 124 has a length of approximately 1 to 2 m. Therefore, there may be a case where the bending of secondary catheter 124 is only stretched and the tip thereof will not move even if secondary catheter 124 is moved back. There may also be the case where the moving amount of secondary catheter 124, even if the tip moves, is trivial. In this case, it is possible that, when secondary catheter 124 are advanced, the tip portion of secondary catheter 124 is located at the same position again. Delivery wire 110 cannot be inserted in either case.

Therefore, when moving back and advancement of secondary catheter 124 are repeated by a predetermined number of times (YES at S50), the distance of moving back and advancement of secondary catheter 124 is increased by just a predetermined distance (S52).

Subsequently, secondary catheter driving unit 20 is controlled such that secondary catheter 124 is moved back by just the predetermined distance (S24). Further, secondary catheter driving unit 20 is controlled such that secondary catheter 124 is advanced by just a predetermined distance (S26).

Accordingly, the position of the tip of secondary catheter 124 in the aneurysm can be altered. Then, the current value of motor 16 of delivery wire driving unit 10, i.e. the torque of motor 16, is set such that delivery wire 110 is inserted by a predetermined insertion force (S10). Thus, the aneurysm can be filled evenly with platinum coil 100.

When secondary catheter 124 is moved more than several mm, for example, there is a possibility of the tip of secondary catheter 124 exiting from aneurysm 42. Therefore, when the distance of moving back and advancement of secondary catheter 124 reaches a predetermined length (YES at S54), a determination is made that insertion of delivery wire 110 is not possible, and insertion of delivery wire 110 is stopped (S40). In other words, insertion of platinum coil 100 is stopped. Thus, exit of the tip of secondary catheter 124 from aneurysm 42 can be prevented.

Third Embodiment

A third embodiment of the present invention will be described hereinafter. The present embodiment differs from the previous first and second embodiments in that delivery wire 110 is advanced while secondary catheter 124 is moved back, and delivery wire 110 is moved back while secondary catheter 124 is advanced. The remaining configuration is similar to that of the previous first or second embodiment. Therefore, detailed description thereof will not be repeated.

Figure 8:
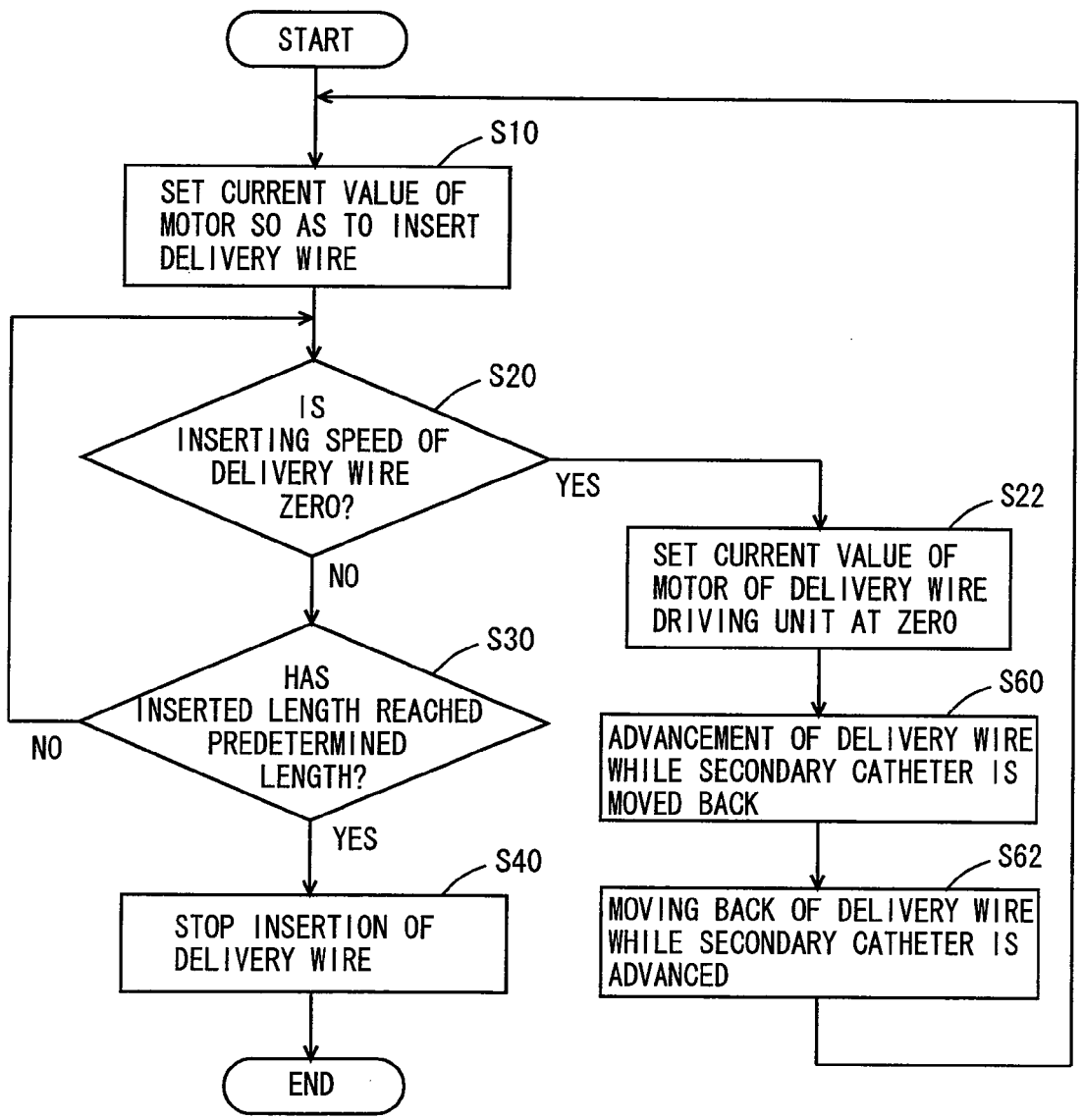
FIG. 8 is a flowchart of the control structure of a program executed by a control circuit according to a third embodiment.

A control structure of the program executed by control circuit 30 according to the present embodiment will be described with reference to FIG. 8. The processes identical to those in the program of the previous first embodiment have the same step number allotted. Therefore, detailed description thereof will not be repeated.

At S60, control circuit 30 controls secondary catheter driving unit 20 and delivery wire driving unit 10 such that secondary catheter 124 is moved back by just a predetermined distance, and delivery wire 110 is advanced while secondary catheter 124 is moved back.

At S62, control circuit 30 controls secondary catheter driving unit 20 and delivery wire driving unit 10 such that secondary catheter 124 is advanced by just a predetermined distance, preferably a distance equal to the moved back distance, and delivery wire 110 is moved back while secondary catheter 124 is advanced. An operation of the coil insertion device according to the present embodiment, based on the configuration and flowchart set forth above, will be described hereinafter.

When the rotating speed of feeding roller 14 of delivery wire driving unit 10, i.e. the inserting speed of delivery wire 110, becomes zero (YES at S20), and the current value of motor 16 of delivery wire driving unit 10 is set at zero (S22), secondary catheter driving unit 20 and delivery wire driving unit 10 are controlled such that secondary catheter 124 is moved back by just a predetermined distance, and delivery wire 110 is advanced while secondary catheter 124 is moved back (S60).

Accordingly, moving back of delivery wire 110 in conjunction with secondary catheter 124 can be prevented. Thus, the position of platinum coil 100 inserted in the aneurysm can be left unchanged.

Further, secondary catheter driving unit 20 and delivery wire driving unit 10 are controlled such that secondary catheter 124 is advanced by just a predetermined distance, and delivery wire 110 is moved back while secondary catheter 124 is advanced (S62).

Accordingly, the advancement of delivery wire 110 in conjunction with secondary catheter 124 can be prevented. Therefore, platinum coil 100 can be located inside secondary catheter 124 when secondary catheter 124 is advanced. Thus, the position of platinum coil 100 can be maintained.

Fourth Embodiment

A fourth embodiment of the present invention will be described hereinafter. The present embodiment differs from the previous first to third embodiments in that the insertion force of delivery wire 110 is reduced when the rotating speed of feeding roller 14 of delivery wire driving unit 10, i.e. the inserting speed of delivery wire 110, is higher than a predetermined speed. The remaining configuration is similar to one of the previous first to third embodiments. Therefore, detailed description thereof will not be repeated.

Figure 9:
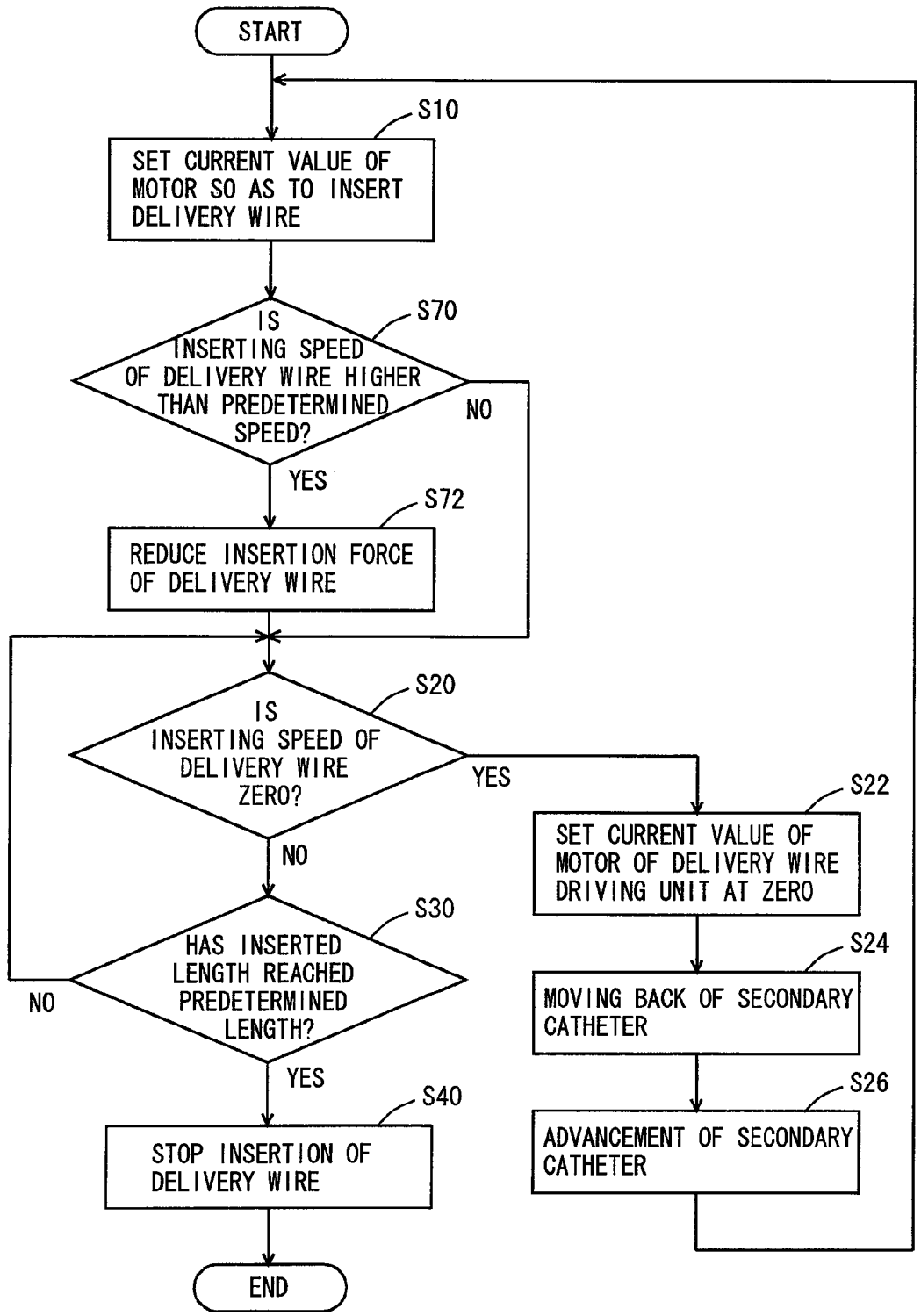
FIG. 9 is a flowchart of the control structure of a program executed by a control circuit according to a fourth embodiment.

A control structure of the program executed by control circuit 30 of the present embodiment will be described hereinafter with reference to FIG. 9. The processes identical to those in the program of the previous first embodiment have the same step number allotted. Therefore, detailed description thereof will not be repeated.

At S70, control circuit 30 determines whether the rotating speed of feeding roller 14 of delivery wire driving unit 10, i.e. the inserting speed of delivery wire 110, is higher than a predetermined speed or not. When the rotating speed of feeding roller 14 of delivery wire driving unit 10 is higher than the predetermined speed (YES at S70), control proceeds to S72; otherwise (NO at S70), control proceeds to S20.

At S72, control circuit 30 reduces the current value of motor 16, i.e. the insertion force of delivery wire 110, by just a predetermined value.

An operation of the coil insertion device according to the present embodiment, based on the configuration and flowchart set forth above, will be described hereinafter.

In the case where the inserting resistance of delivery wire 110 is extremely low as compared with the insertion force when delivery wire 110 is to be inserted, delivery wire 110 will be inserted at high speed. If the rotating speed of feeding roller 14 of delivery wire driving unit 10 is high, the travel of delivery wire 110 cannot follow the rotation, causing the occurrence of slippage between delivery wire 110 and feeding roller 14.

In this case, measurement of the traveling distance of delivery wire 110 based on encoder 18 rotating integrally with feeding roller 14 (or motor 16) of delivery wire driving unit 10 cannot be carried out. Therefore, the rotation of feeding roller 14 must be suppressed to a speed where slippage between delivery wire 110 and feeding roller 14 does not occur.

To this end, when the rotating speed of feeding roller 14 of delivery wire driving unit 10, i.e. the inserting speed of delivery wire 110, is higher than a predetermined speed (YES at S70), the current value of motor 16, i.e. the insertion force of delivery wire 110, is reduced such that the inserting speed of delivery wire 110 attains the predetermined speed (S72).

Thus, slippage between feeding roller 14 feeding out delivery wire 110 and delivery wire 110 can be suppressed. As a result, the inserted length of delivery wire 110 can be calculated with favorable accuracy from the number of rotations or the like of feeding roller 14.

Fifth Embodiment

A fifth embodiment of the present invention will be described hereinafter. The present embodiment differs from the previous first to fourth embodiments in that the insertion force of delivery wire 110 is obtained based on the bending degree of delivery wire 110. The remaining configuration is similar to one of the previous first to fourth embodiments. Therefore, detailed description thereof will not be repeated.

Figure 10:
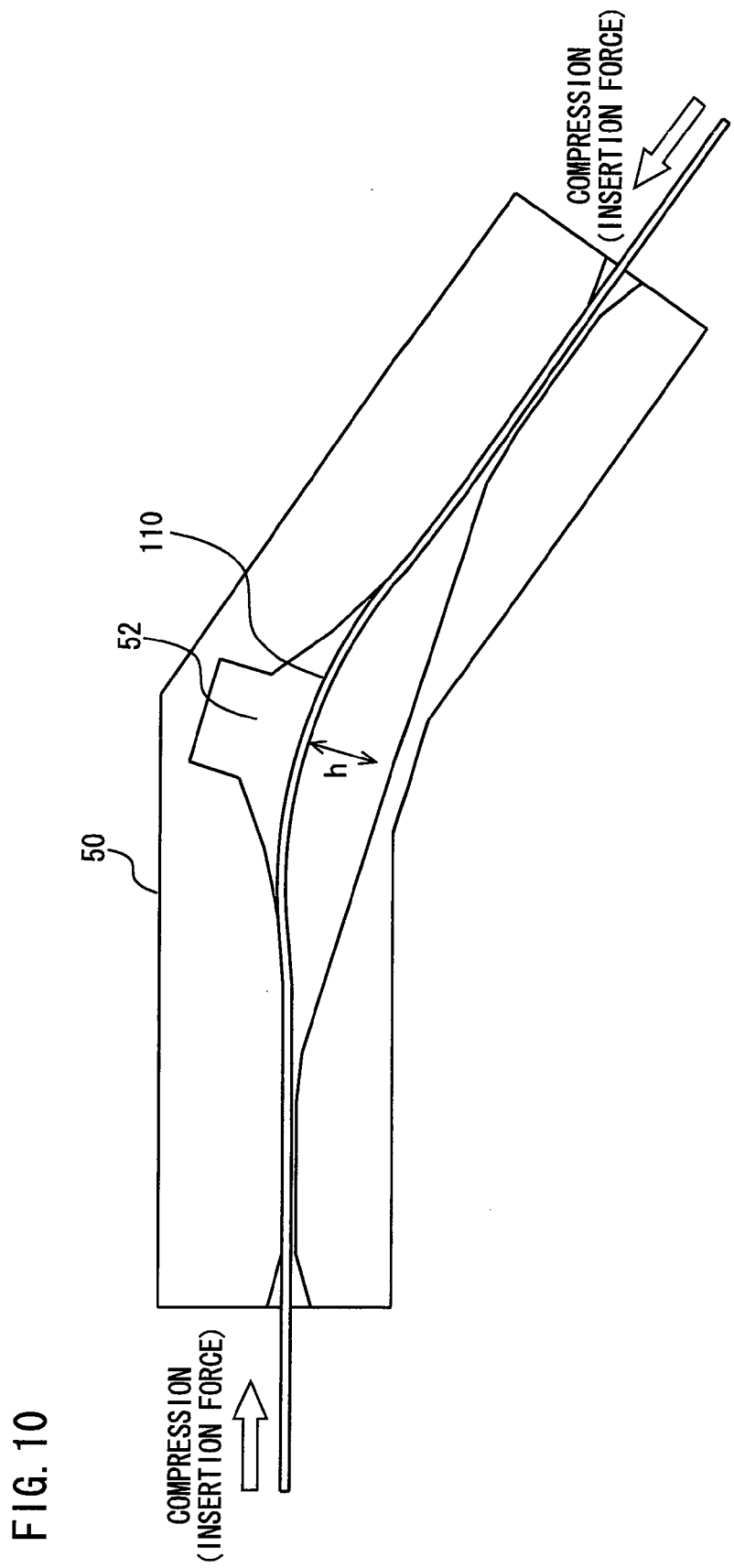
FIG. 10 is a sectional view of a bending measurement instrument.

As shown in FIG. 10, an insertion device of a coil according to the present embodiment further includes a bending measurement instrument 50. Bending measurement instrument 50 is arranged in lieu of or incorporated in Y connector 131 in which delivery wire 110 is inserted. Bending measurement instrument 50 is a curved pipe having a space 52 at the central area. Delivery wire 110 is inserted into bending measurement instrument 50 while yielding along one wall.

When compression acts on delivery wire 110, delivery wire 110 is curved at space 52 in bending measurement instrument 50. The height h of the mountain of the curve increases in accordance with the bending of delivery wire 110.

Bending measurement instrument 50 includes an optical sensor constituted of, for example, a light source that emits light (infrared LED or the like), and a light receiver (phototransistor or the like) arranged at a position facing the light source. The bending degree (the height h of the mountain of the curve) of delivery wire 110 is detected by means of the sensor. The method of measuring the bending degree of delivery wire 110 is not limited to the aforementioned method.

A signal representing the bending degree of delivery wire 110 measured by bending measurement instrument 50 is applied to control circuit 30. Control circuit 30 calculates the insertion force of delivery wire 110 based on the correlation between the bending degree of delivery wire 110 and the compression acting on delivery wire 110 (insertion force of delivery wire 110) that is determined in advance.

Thus, the insertion force of delivery wire 110 can be calculated with favorable accuracy from the bending degree of delivery wire 110. Accordingly, the insertion force of delivery wire 110 can be controlled with favorable accuracy by feedback control, or the like.

Alternatively, the actual current value supplied to motor 16 that drives feeding roller 14 of delivery wire driving unit 10 may be measured to calculate the insertion force of delivery wire 110 based on the correlation between the current value and the compression acting on delivery wire 110 (insertion force of delivery wire 110).

Sixth Embodiment

A sixth embodiment of the present invention will be described hereinafter. The present embodiment differs from the previous first to fifth embodiments in that delivery wire driving unit 10 and secondary catheter driving unit 20 can be controlled such that delivery wire 110 and secondary catheter 124 are inserted according to manipulation by a surgeon or the like through the usage of master device 60. The remaining configuration is similar to one of the previous first to fifth embodiments. Therefore, detailed description thereof will not be repeated.

Figure 11:
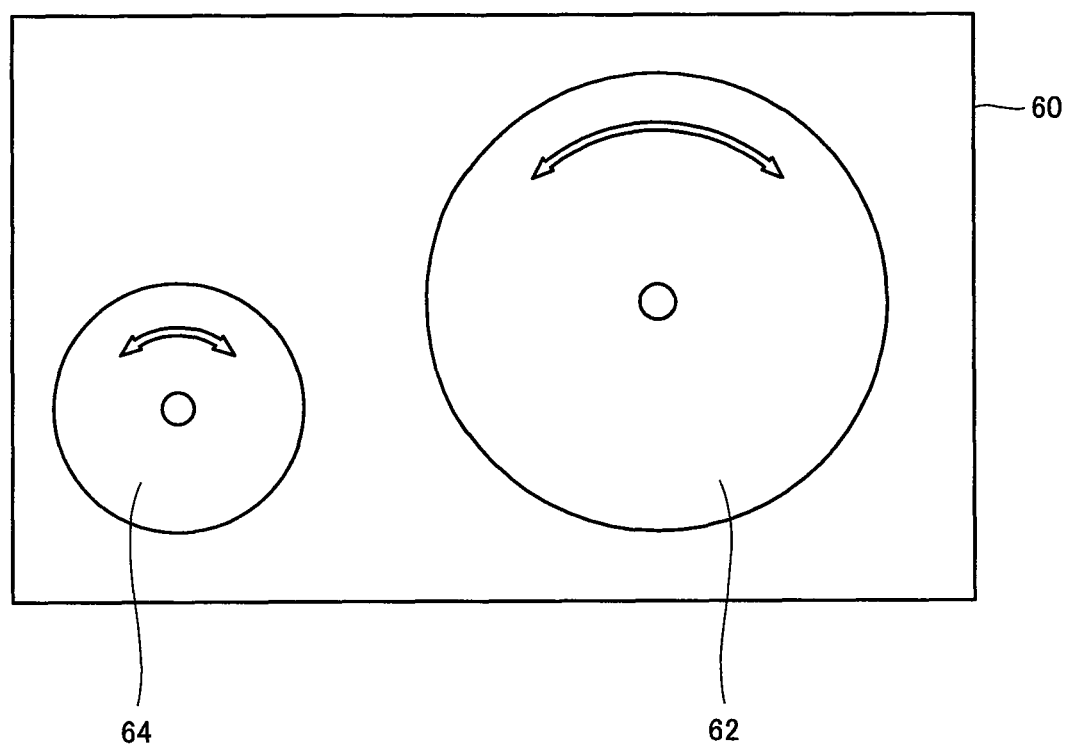
FIG. 11 represents a schematic configuration of an insertion device of a coil to which a master device is connected.
Figure 12:
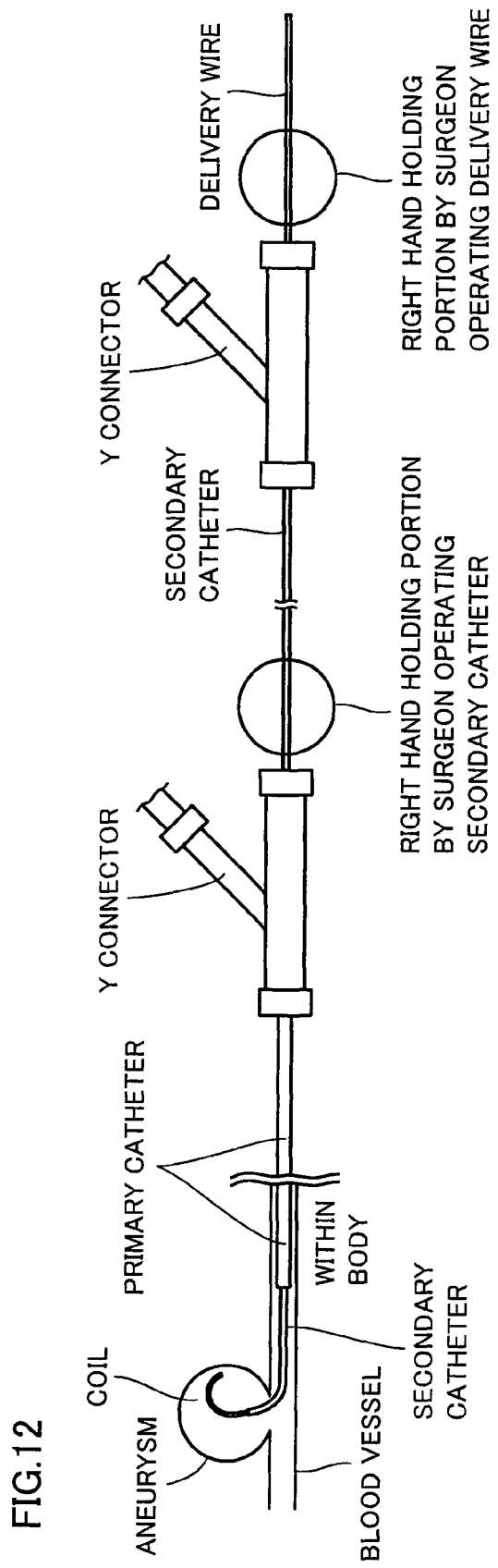
FIG. 12 represents a medical instrument employed in coil embolization treatment.

As shown in FIG. 11, the coil insertion device of the present embodiment includes a master device 60 that can be connected to control circuit 30. Master device 60 controls delivery wire driving unit 10 and secondary catheter driving unit 20 such that delivery wire 110 and secondary catheter 124 are inserted according to manipulation by a surgeon or the like. Instead of control circuit 30, master device 60 may be connected to delivery wire driving unit 10 and secondary catheter driving unit 20.

Master device 60 includes, for example, a dial type delivery wire manipulation unit 62 and a secondary catheter manipulation unit 64. Master device 60 controls delivery wire driving unit 10 such that delivery wire 110 is inserted (advanced) and moved back by just a distance according to the rotation of delivery wire manipulation unit 62. Master device 60 also controls secondary catheter driving unit 20 such that secondary catheter 124 is inserted and moved back by just a distance according to the rotation of secondary catheter manipulation unit 64.

Accordingly, secondary catheter 124 and delivery wire 110 can be inserted according to manipulation by, for example, a surgeon or the like, likewise with a conventional master slave apparatus.

Other Embodiments

The previous first to sixth embodiments may be combined arbitrarily.

It should be understood that the embodiments disclosed herein are illustrated and non-restrictive in every respect. The scope of the present invention is defined by the terms of the claims, rather than the description set forth above, and is intended to include any modification within the scope and meaning equivalent to the terms of the claims.

The invention claimed is:

1. An insertion device of a coil attached to a tip of a delivery wire, comprising:
   a catheter;
   a delivery wire inserted into said catheter;
   a first driving unit moving the catheter into which said delivery wire is inserted;
   a second driving unit moving said delivery wire;
   a bending measuring instrument into which said delivery wire is inserted; and
   a control unit programmed to control said second driving unit so as to insert said delivery wire by a predetermined insertion force, to control said first driving unit such that said catheter is advanced after said catheter is moved back if said delivery wire cannot be inserted under a state where said second driving unit is controlled so as to insert said delivery wire by said predetermined insertion force, and to control said second driving unit such that said delivery wire is inserted by said predetermined insertion force after said catheter is advanced, wherein
   said second driving unit moves said delivery wire through a rotation of a motor, and
   said control unit calculates an insertion force of said delivery wire from a bending degree of said delivery wire measured by the bending measuring instrument.

2. The insertion device of a coil according to claim 1, wherein said control unit controls said first driving unit and said second driving unit such that said delivery wire is advanced while said catheter is moved back, and said delivery wire is moved back while said catheter is advanced.

3. The insertion device of a coil according to claim 1, wherein said control unit increases a distance of moving back and advancement of said catheter, if moving back and advancement of said catheter are repeated by a predetermined number of times.

4. The insertion device of a coil according to claim 3, wherein said control unit stops insertion of said delivery wire when the distance of moving back and advancement of said catheter reaches a predetermined distance.

5. The insertion device of a coil according to claim 1, wherein said control unit reduces an insertion force of said delivery wire when a speed of inserting said delivery wire is higher than a predetermined speed.

6. The insertion device of a coil according to claim 1, wherein said control unit stops insertion of said delivery wire when an inserted length of said delivery wire reaches a predetermined length.

7. The insertion device of a coil according to claim 1, further comprising a device, instead of said control unit, controlling said first driving unit and said second driving unit according to manipulation by an operator.

8. The insertion device of a coil according to claim 1, wherein the bending measuring instrument comprises a curved pipe wherein an internal portion of the pipe has a first cross sectional area at an entrance region of the pipe and a second cross sectional area in a central region of the pipe, wherein the second cross sectional area is greater than the first cross sectional area.

9. An insertion method of a coil attached to a tip of a delivery wire, wherein a first driving unit moving a catheter into which a delivery wire is inserted and a second driving unit moving said delivery wire are disposed, said insertion method comprising the steps of:
controlling said second driving unit so as to insert said delivery wire by a predetermined insertion force,
controlling said first driving unit such that said catheter is advanced after said catheter is moved back if said delivery wire cannot be inserted under a state where said second driving unit is controlled so as to insert said delivery wire by said predetermined insertion force and
controlling said second driving unit such that said delivery wire is inserted by said predetermined insertion force after said catheter is advanced, wherein
said second driving unit moves said delivery wire through a rotation of a motor, and
a control unit calculates the insertion force of said delivery wire from a bending degree of said delivery wire.

10. An insertion device of a coil attached to a tip of a delivery wire, comprising:
a catheter;
a delivery wire inserted into said catheter;
first driving means for moving the catheter into which said delivery wire is inserted;
second driving means for moving said delivery wire;
a bending measuring instrument into which said delivery wire is inserted; and
a control unit programmed to control said second driving means so as to insert said delivery wire by a predetermined insertion force, to control said first driving means such that said catheter is advanced after said catheter is moved back if said delivery wire cannot be inserted under a state where said second driving means is controlled so as to insert said delivery wire by said predetermined insertion force, and to control said second driving means such that said delivery wire is inserted by said predetermined insertion force after said catheter is advanced, wherein
said second driving unit moves said delivery wire through a rotation of a motor, and
said control unit calculates an insertion force of said delivery wire from a bending degree of said delivery wire measured by the bending measuring instrument.

11. The insertion device of a coil according to claim 10, wherein the bending measuring instrument comprises a curved pipe wherein an internal portion of the pipe has a first cross sectional area at an entrance region of the pipe and a second cross sectional area in a central region of the pipe, wherein the second cross sectional area is greater than the first cross sectional area.

* * * * *